(12) United States Patent
Webb et al.

(10) Patent No.: US 6,843,805 B2
(45) Date of Patent: *Jan. 18, 2005

(54) INTERVERTEBRAL IMPLANT

(75) Inventors: John Webb, Nottingham (GB); Inga Maren Häfeli-Knothe, Pieterlen (CH); Thomas Häfeli, Grenchen (CH); Alfred Benoit, Lengnau (CH)

(73) Assignee: Synthes (U.S.A.), Paoli, PA (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/337,267

(22) Filed: Jan. 7, 2003

(65) Prior Publication Data

US 2003/0114932 A1 Jun. 19, 2003

Related U.S. Application Data

(63) Continuation of application No. 09/254,206, filed as application No. PCT/CH96/00303 on Sep. 4, 1996, now Pat. No. 6,503,279.

(51) Int. Cl.[7] .............................. A61F 2/44; A61B 17/70
(52) U.S. Cl. ................................ 623/17.16; 623/17.11; 623/16.11; 606/61
(58) Field of Search ...................... 623/17.11–17.16, 623/16.11, 23.5–23.6

(56) References Cited

U.S. PATENT DOCUMENTS

| | | | |
|---|---|---|---|
| 4,683,161 A | 7/1987 | Rice et al. ................. 428/178 |
| 4,834,757 A * | 5/1989 | Brantigan ................ 623/17.11 |
| 5,002,576 A | 3/1991 | Fuhrmann et al. ............. 623/17 |
| 5,306,303 A | 4/1994 | Lynch ......................... 623/16 |
| 5,306,309 A | 4/1994 | Wagner et al. ................ 623/17 |
| 5,645,596 A | 7/1997 | Kim et al. .................... 623/17 |
| 5,888,222 A | 3/1999 | Coates et al. ............. 623/17.16 |
| 5,989,289 A | 11/1999 | Coates et al. ................. 623/17 |
| 6,241,771 B1 * | 6/2001 | Gresser et al. ........... 623/17.16 |

FOREIGN PATENT DOCUMENTS

| | | |
|---|---|---|
| DE | 4423826 A1 | 1/1995 |
| EP | 0 346 269 B1 | 12/1989 |
| EP | 0 493 698 A1 | 7/1992 |
| EP | 0 505 634 A1 | 9/1992 |
| FR | 2 703 580 A1 | 10/1994 |
| WO | WO 88/03417 | 5/1988 |

* cited by examiner

Primary Examiner—David J Isabella
(74) Attorney, Agent, or Firm—Jones Day

(57) ABSTRACT

The present invention relates to an intervertebral implant for fusion of vertebrae. The implant has top and bottom surfaces configured and dimensioned to contact end plates of the vertebrae and a jacket forming a side surface of the implant and having a three-dimensional texture for promoting initial stability. The implant is made of a porous ceramic material. The implant according to this invention is characterized in that upon primary fusion during the resorption process, it equalizes the distance (corresponding to intervertebral disk height) between two vertebrae while providing adequate fusion and is resorbed by the body after a certain amount of time.

19 Claims, 1 Drawing Sheet

INTERVERTEBRAL IMPLANT

This is a continuation of application Ser. No. 09/254,206 filed Mar. 3, 1999 now U.S. Pat. No. 6,503,279 which is a national stage of PCT application No. PCT/CH96/00303 filed Sep. 4, 1996.

FIELD OF THE INVENTION

This invention relates to an intervertebral implant for use in spinal fusion.

BACKGROUND OF THE INVENTION

Intervertebral implants of this type are inserted when, after removal of the intervertebral disk between two vertebrae (especially in the lumbar section of the vertebral column), the vertebrae are to be fused. One or two such implants are used in each intervertebral space.

In EP-B 346.269, FUHRMANN ET AL already describe an intervertebral implant whose outside front, end and lateral surfaces are coated with a layer of hydroxyl apatite or a ceramic HIP material. The drawback of this earlier implant lies in the fact that the basic body of the implant consists of typical nonceramic and hence nonresorbable materials.

In U.S. Pat. No. 5,306,303, LYNCH describes an intervertebral implant which consists entirely of a porous ceramic material. The drawback of that earlier implant concept lies, on the one hand, in its low pressure resistance attributable to the relatively high porosity and, on the other hand, in the fact that the implant cannot be filled with bone chips with which to obtain accelerated bone integration.

Another intervertebral implant has been described in EP 505 634 by OKA et al, consisting of a porous ceramic base element with hydrogel deposited in the pores. This earlier implant as well offers insufficient pressure resistance owing to the hydrogel-filled pores.

In EP-A-493 698, HARLE describes a bone substitute for filling fault areas, consisting of two different, porous, ceramic materials having pores which are evacuated.

Finally, DE-A 44 23 826 by ASAHI describes an artificial ceramic vertebra, the porosity of which is maintained by means of a foaming agent.

SUMMARY OF THE INVENTION

This invention is intended to solve the problem. One objective is to provide an intervertebral implant that can hold up to the various pressures to which the vertebral column is exposed, offering a sufficiently large contact surface at the end plates so as to prevent them from sinking in. It is also designed to permit fastest possible fusion of the two vertebrae as well as rapid incorporation of the implant with due allowance for the height of the intervertebral disk prior to its removal. In a subsequent progression, the implant should be fully (or nearly fully) capable of being replaced by the patient's own bone growth.

The present invention relates to an intervertebral implant for fusion of vertebrae. The implant has top and bottom surfaces configured and dimensioned to contact end plates of the vertebrae and a jacket forming a side surface of the implant and having a three-dimensional texture for promoting initial stability. The implant is made of a porous ceramic material.

Advantageously, this makes it possible for the implant according to this invention, upon primary fusion during the resorption process, to equalize the distance (corresponding to intervertebral disk height) between two vertebrae while providing adequate fusion and to be resorbed by the body after a certain amount of time to a point where it is no longer detectable.

Another major advantage of this implant is its transparency to xrays, which avoids artifacts that would interfere with a diagnosis of the surrounding bone structure.

The intervertebral implant may be shaped as a prismatic or as a cylindrical element, with a porosity not to exceed 30% by volume. In one preferred enhanced embodiment of this invention, the porosity of the ceramic material is 9 vol. % at the most and preferably not more than 5 vol. %. Reduced porosity of the implant provides greater pressure resistance which is a fundamental requirement especially in the lumbar section of the vertebral column. In this area, particular importance is attributed to the largest possible contact surface between the end plate and the implant. Therefore, the wall thickness of the ring-shaped intervertebral implant should be at least 4 mm and preferably at least 6 mm so as to inhibit any penetration, of the implant into the end plates.

In another preferred embodiment of this invention, the ceramic material has a density value of greater than 2.8 and preferably greater than 3.1, which further enhances the pressure resistance of the implant.

The implant is preferably configured as a hollow, circular cylinder which permits the insertion of the patient's own bone chips or similar biocompatible material, thus promoting rapid fusion of the implant.

In another preferred embodiment of this invention, the top surface and/or the bottom surface of the implant is not planar but is provided with grooves and/or ridges extending perpendicular to the axis of the cylinder. Such three-dimensional structuring of the top and bottom surface would permit primary fastening of the implant immediately after its introduction in the intervertebral space, thus enhancing the positional stability of the implant and the rotational stability of the adjoining vertebrae. The three-dimensional surface structure is preferably in the form of "undulations" (raised reinforcing ridges with distinct radii) in both the longitudinal and horizontal directions.

Depending on where the implant is applied, the top and/or bottom surface extend parallel or in wedge-like converging fashion in relation to each other so as to permit adequate following of the curvature (lordosis, kyphosis).

The implant is preferably provided with a convex top and/or bottom surface which matches the concave shape of the natural end plates of the vertebrae, to achieve better contact between the implant and the end plates.

The outer surface jacketing the intervertebral implant is preferably provided with one or several perforations primarily for the purpose of engaging an instrument for manipulating the implant. The perforations may be located both on the anterior side and in the lateral zone of the implant. The perforations additionally serve to facilitate primary bone growth through the implant.

The positional stability of the implant can be further improved by providing the jacket of the intervertebral implant with a fine, three-dimensional texture which promotes bonding with the bone at an early stage. This texture is preferably 0.5–1.0 mm deep, with grooves 0.5 to 1.0 mm wide. The entire surface of the jacket may be textured in that fashion.

For the implant according to this invention, suitable, ceramic materials may be used which have typically and successfully been used in medicine, except with a porosity as defined by this invention, with preference given to polycrystalline ceramics with a foreign-phase content or impurities of less than 3 and preferably less than 2% by weight. The pressure resistance of the ceramic material should be between 400 and 600 MPa and preferably between 450 and 550 Mpa.

BRIEF DESCRIPTION OF THE DRAWINGS

The following will describe the invention and its enhanced implementations in more detail with the aid of a partly schematic illustration of an embodiment shown by way of example.

Shown in FIG. 1 is a perspective view of the implant according to this invention.

DETAILED DESCRIPTION OF THE PREFERRED EMBODIMENTS

Figure 1:
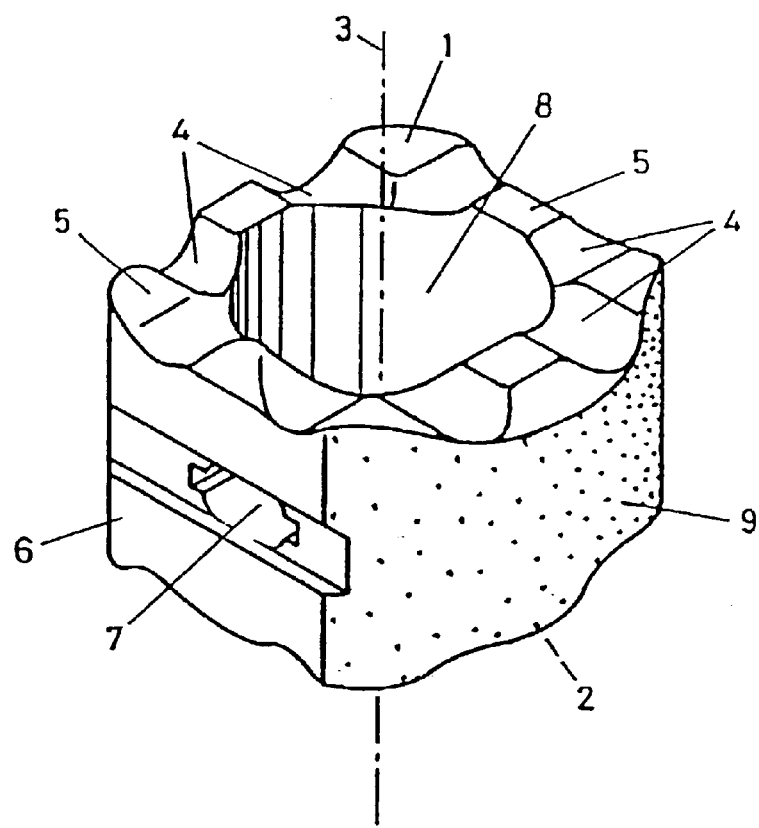

The intervertebral implant illustrated in FIG. 1 consists essentially of a hollow cylinder with an inner space 8, a longitudinal axis 3, a top surface 1 and a bottom surface 2. The intervertebral implant is essentially produced from a polycrystalline ceramic material. The ceramic material has a porosity of 5 vol. %, the pores are filled with air. The width of the pores is less than 100 μm and preferably less than 50 μm. The foreign-phase content of the ceramic material is 1.5% by weight. The pressure resistance of the ceramic material is 500 Mpa.

The top and bottom surfaces 1, 2 serve to provide bone contact with the surface plates of two vertebrae and are configured accordingly. The wall thickness of the intervertebral implant is 7 mm, the density of the ceramic material is 3.2. The top surface 1 and the bottom surface 2 are not planar but are provided with a number of grooves 4 and ridges 5 extending in a perpendicular (i.e. radial) direction relative to the longitudinal axis 3.

The top surface 1 and the bottom surface 2 extend in wedge-like converging fashion in relation to each other and have a slightly convex outward curvature.

The anterior side of the outer surface 6 jacketing the intervertebral implant is provided with a perforation 7 serving to accept a manipulating instrument. The jacket is further provided with a three-dimensional surface texture 9 having a depth of 0.75 mm.

The following will describe in detail the clinical application of the intervertebral implant according to this invention.

The implant illustrated in the figure is filled with bone chips (bone graft or bone substitutes), possibly compressed, grasped with a suitable instrument by insertion in the perforation 7 and introduced into the appropriately cleared-out intervertebral space with the aid of a distractor device.

What is claimed is:

1. An intervertebral implant for fusion of vertebrae comprising:
   top and bottom surfaces configured and dimensioned to contact end plates of the vertebrae; and
   an outer side surface substantially extending from the top surface to the bottom surface with an additional three-dimensional texture added thereto for promoting initial stability;
   wherein the implant is formed of a resorbable material; and
   wherein the three dimensional texture comprises openings on the outer side surface having a depth from about 0.5 mm to about 1 mm.

2. The implant of claim 1 wherein the implant has a substantially cylindrical shape extending along a longitudinal axis.

3. The implant of claim 1 wherein the implant has a bore extending from the top surface to the bottom surface that forms an interior for receiving a bone grafting material.

4. The implant of claim 1 wherein the resorbable material has a porosity of less than about 30 vol. %.

5. The implant of claim 1 wherein the resorbnble material has a porosity of less than about 5 vol. %.

6. The implant of claim 1 wherein the resorbable material has pores that are open.

7. The implant of claim 6 wherein the pores have a width of less than about 100 μm.

8. The implant of claim 1 wherein the three dimensional texture further comprises grooves having a width of about 0.5 mm to about 1 mm.

9. The implant of claim 1 wherein at least one of the top and bottom surfaces comprises a plurality of grooves and ridges for promoting initial stability of the implant.

10. The implant of claim 1 further comprising at least one hole for receiving a surgical instrument for manipulating the implant.

11. The implant of claim 1 further comprising a bore extending from the top surface toward the bottom surface and forming an inner surface, with a wall defined between the outer side surface and the inner surface having a thickness of at least about 6 mm.

12. The implant of claim 1 wherein the resorbable material has a density of greater than about 2.8 g/cm$^3$.

13. The implant of claim 1 wherein the resorbable material is a polycrystalline ceramic.

14. The implant of claim 13 wherein the ceramic has an impurity content of less than about 3% by weight.

15. The implant of claim 13 wherein the ceramic has a compressive strength from about 400 MPa to about 600 MPa.

16. The implant of claim 1 wherein the resorbable material is radiolucent.

17. An intervertebral implant for fusion of vertebrae comprising:
   top and bottom surfaces configured and dimensioned to contact end plates of the vertebrae; and
   an outer side surface substantially extending from the top surface to the bottom surface with an additional three-dimensional texture added thereto for promoting initial stability;
   wherein at least one of the top and bottom surfaces is not planar and the implant is formed of a resorbable material having a porosity of less than about 30 vol. %; and
   wherein the three dimensional texture comprises openings on the outer side surface having a depth from about 0.5 mm to about 1 mm.

18. The implant of claim 17 wherein the resorbable material is ceramic.

19. An intervertebral implant for fusion of vertebrae comprising:
   a body made of a resorbable material, the body having top and bottom surfaces configured and dimensioned to contact end plates of the vertebrae, and the body having an outer side surface substantially extending from the top surface to the bottom surface, wherein the outer side surface has additional three-dimensional texturing added thereto for promoting initial stability comprising openings with a depth from about 0.5 mm to about 1 mm.

* * * * *